United States Patent [19]

Malloy et al.

[11] 4,243,831

[45] Jan. 6, 1981

[54] REMOVAL OF PEROXIDES AND COLOR BODIES FROM INTERNAL OLEFINS BY SOLID ADSORBENTS

[75] Inventors: Thomas P. Malloy, Lake Zurich; George W. Lester, Hoffman Estates, both of Ill.

[73] Assignee: UOP Inc., Des Plaines, Ill.

[21] Appl. No.: 62,097

[22] Filed: Jul. 30, 1979

[51] Int. Cl.$^3$ ................................................ C07C 7/12
[52] U.S. Cl. ........................................ 585/824; 585/820; 585/823
[58] Field of Search ...................... 585/823, 824, 820

[56] References Cited

U.S. PATENT DOCUMENTS

| | | | |
|---|---|---|---|
| 3,420,906 | 1/1969 | Singleterry | 585/824 |
| 3,629,352 | 12/1971 | Hoover | 585/824 |
| 3,801,669 | 4/1974 | Christmann | 585/824 |
| 3,821,314 | 6/1974 | Arkell et al. | 585/824 |

Primary Examiner—Curtis R. Davis
Attorney, Agent, or Firm—James R. Hoatson, Jr.; Raymond H. Nelson; William H. Page, II

[57] ABSTRACT

A process for the reduction of the peroxide number and color of olefins comprises contacting the olefin with an adsorbent and separating the contacted olefin from the adsorbent. The process is effective for internal olefins, a class of olefins in which reduction of peroxide number by conventional means is ineffective. Examples of effective adsorbents which may be employed in the process includes charcoal, alumina, silica, diatomaceous earth and montmorillonite clays.

2 Claims, No Drawings

REMOVAL OF PEROXIDES AND COLOR BODIES FROM INTERNAL OLEFINS BY SOLID ADSORBENTS

BACKGROUND OF THE INVENTION

Olefins, which are important articles of commerce, upon storage and exposure to air tend to form peroxides, hydroperoxides, and other oxidized, unstable materials whose presence can be detected by analytical procedures such as determining the so-called peroxide number. Such peroxidic materials are dangerous in themselves because of their instability, and their presence may even lead to explosions. In addition to posing a safety hazard, build-up of peroxidic materials may render the olefins unsuitable for further use, e.g., as raw materials for sulfonation leading to detergents. Finally, formation of peroxidic materials frequently is associated with a significant undesirable darkening of olefins. The color often is carried along in production of other materials of commerce, and the resulting products are less desirable, and sometimes even unacceptable, because of their darker color. Removal of such color bodies from materials made from darkened olefins is often difficult and expensive, hence there is a necessity for providing olefins as light in color as is possible.

Removal of peroxidic material from alpha-olefins, i.e., linear, unbranched olefins having a terminal methylene group, commonly is performed using a single- or multi-stage wash with sodium bisulfate, or, alternatively, distilling the olefin from sulfuric acid. However, it has been found that neither method is satisfactory to reduce the peroxide number of internal olefins, whether branched or unbranched. It also has been found that unbranched internal olefins form peroxidic materials more readily than alpha-olefins, and branched internal olefins having a tertiary allylic hydrogen atom, i.e., with the structural unit $R_1R_2CH$—C═C—$R_3$, where $R_1$-$R_3$ are alkyl groups, are still more susceptible to formation of peroxidic materials with concomitant darkening. The internal olefins pose the dilemma of becoming darker and forming peroxidic materials faster than do alpha-olefins, while being more resistant to removal of color bodies and peroxidic materials than is the case for alpha-olefins.

SUMMARY OF THE INVENTION

This invention relates to the discovery that certain solid adsorbents effectively reduce the peroxide number of interal olefins with a simultaneous reduction of color. An object of the invention is to reduce the peroxide number and color of olefins, especially internal olefins. An embodiment of the invention is the process for reducing the peroxide number and color of olefins which comprises contacting the olefin with a solid adsorbent and separating the contacted olefin. A more specific embodiment is application of the process wherein the olefin is an internal olefin, and the adsorbent is selected from the group consisting of charcoal, alumina, silica, kaolin minerals, diatomaceous earth and montmorillonite clay.

Other objects and embodiments will be apparent from the detailed description which follows.

DESCRIPTION OF THE INVENTION

The process of this invention may be applied to any olefin, but preferably olefinic hydrocarbons, and preferably internal aliphatic olefins. In one embodiment the olefins which may be subjected to a process for the removal of peroxides are linear in nature, contain from about 8 to about 20 carbon atoms, are internal olefins, and are readily available from dehydrogenation of alkenes. Examples of such aliphatic olefins, which are merely representative of the class and which are not to be construed as a limitation thereof, include 2-octene, 3-octene, 4-octene, 2-nonene, 3-nonene, 4-nonene, 2-hexadecene, 3-hexadecene, 4-hexadecene, 5-hexadecene, 6-hexadecene, 7-hexadecene, 8-hexadecene, 2-eicosene, 3-eicosene, 4-eicosene, and the other isomeric eicosenes through and including 10-eicosene.

In another embodiment the olefins which may comprise the feedstock of the present invention will contain from about 6 to about 18 carbon atoms, the carbon chain is branched, and the olefins are internal olefins. This class of olefins is particularly prone to formation of peroxidic materials and is particularly resistant to reduction of peroxide number by conventional means. Examples of such aliphatic olefins representative of the class, but which are not limitations thereof, include 4-methyl-2-pentene, 4,6-dimethyl-2-heptene, 4,6-dimethyl-3-heptene, 4-ethyl-5-methyl-2-hexene and 2,4,5,9-tetramethyl-3,8-diethyl-4-decene. Members of this class of olefins may be formed by oligomerization of olefins, such as propylene, butylene, amylene, hexylene, etc.

The process of this invention may be practised using a broad variety of solid adsorbents as the peroxide-removing material. In using the term "adsorbent" reference is made to materials which commonly are used to remove relatively small amounts of undesirable dissolved components in a liquid mixture, whether such removal is by the process of adsorption or absorbtion. One example of a suitable adsorbent is charcoal, by which is meant any form of carbon, whatever its source, commonly used as an adsorbent. Other examples of adsorbents suitable in this process include alumina, silica, diatomaceous earth, montmorillonite clays, such as bentonite and Fuller's earth, kaolin minerals and products derived from such materials by various treatments such as acid or base treatment. Such examples are given by way of illustration only and are not intended to serve as limitations on suitable adsorbents.

The amount of adsorbent used depends upon the nature of the adsorbent, the peroxide number of the olefin, the contact time and the temperature. Generally, ambient temperature is preferred as an energy conservative variant, but temperatures below ambient, that is, about 10° C., and up to about 80° C. may be employed. The adsorbent may be added at concentrations from about 0.5% to 10% by weight of olefin, with contact time ranging from about 10 minutes to about 100 minutes or more. Shorter contact times are favored by higher concentrations of adsorbents, higher temperatures, and lower peroxide numbers of the olefin feed.

The method of contacting the absorbent in olefin is not critical. Thus, a batch process may be used wherein the adsorbent is effectively contacted by mixing with olefin and, after a period of time, separating the olefin from the adsorbent by suitable means, for example, by filtration, decantation, centrifugation, etc. The process of the invention may also be conducted in a continuous or semi-continuous fashion. For example, the olefin may be pumped from a storage tank through a fixed bed of the adsorbent. The feed rate is adjusted for the kind, amount, and prior use of adsorbent in the bed and the peroxide number of the feedstock so that the contact time of the olefin with the adsorbent is sufficiently long to give an effluent with the desired peroxide number reduction. The effluent may be kept in a holding tank for a short time, or used or shipped immediately. Other variations will be recognized by those skilled in the art.

The process of this invention is quite effective in reducing the color of olefins, by which is meant the Saybolt color as determined by the standard method ANSI/ASTM D156-64. Values of Saybolt color range from +30 (lightest) to −16 (darkest). Reductions in color from about 5 to about 15 units generally may be achieved, and even greater reductions may be achieved in some cases. There is some correlation between Saybolt color and carbonyl value, i.e., a measure of the extent of carbonyl group present in the material, but this correlation is only fair. Since carbonyl groups frequently are associated with color bodies, one could expect that the greater the carbonyl number the darker will be the color of the olefinic materials.

The following examples merely serve to illustrate the process of this invention and it is to be understood that the present invention is not necessarily limited thereto.

EXAMPLES 1–5

In all examples the olefinic feedstock was a mixture of linear internal olefins containing 15 to 18 carbon atoms. Analysis showed the following distribution: C15, 25.0%; C16, 33.3%; C17, 30.0%; C18, 11.7%. The feedstock had a relatively high content of peroxidic materials as determined by its peroxide number. Organic peroxides and hydroperoxides oxidize iodide ion in an acidic medium to iodine. The iodine thus liberated may be titrated with a thiosulfate solution of known normality using a starch indicator. Peroxide number is defined as the number of milliequivalents of iodide ion per liter oxidized by the test substance.

That removal of peroxidic material from the chosen feedstock was difficult using conventional methods is shown by the following. In one experiment the olefinic feed was contacted by stirring with 2% by weight of a saturated aqueous solution of sodium bisulfite at a temperature of about 45° C. for about 30 minutes. In another experiment the olefinic feed was contacted by effective mixing with 2% by weight of concentrated sulfuric acid at about 5° C. for about 15 minutes. The olefins were separated from acid sludge and washed with caustic, excess caustic was removed by a water wash, and the olefins were distilled. In both methods the peroxide number of the treated olefin remained relatively high.

Olefins were treated with adsorbent using the following general procedure. Adsorbent, 50 g, was packed in a fixed bed and the olefinic feed stock was passed through the bed at a back pressure of 6 psig such that the feed rate was 250–500 ml. per hour, depending upon the adsorbent. The adsorbents were activated carbon (Darco DX1-06410), alumina (Amcon alumina base, 10/30 mesh), silica gel (Davison, 60/200 mesh), and calcined silica, fine mesh. Effluent was collected and analyzed for carbon atom distribution, peroxide number, Saybolt color, and carbonyl number. In all cases the carbon atom distribution was unchanged; recovery of olefins was in excess of 95%. Analytical data for the remaining parameters are summarized in the table.

Reduction of Color and Peroxide Number

| Example | Treatment | Peroxide Number | Saybolt Color | Carbonyl Value |
|---|---|---|---|---|
| Feedstock | | 14.5 | +15 | 92 |
| 1. | Bisulfite wash | 10.5 | +12 | 123 |
| 2. | Sulfuric acid wash | 3.8 | −16 | 55 |
| 3. | Activated carbon | 2.0 | +25 | 53 |
| 4. | Alumina | 1.8 | +18 | 17.3 |
| 5. | Silica gel | 0 | +26 | 3.2 |
| 6. | Calcined silica | 0 | +20 | 4.0 |

These data show that a variety of adsorbents are effective in reducing the peroxide number of an olefinic mixture of a type whose peroxide number is substantially unaffected by more conventional means. For example, neither a bisulfite wash nor distillation from sulfuric acid served to reduce the peroxide number of the feedstock below 3.8. In contrast, contacting the same olefinic feed with solid adsorbents reduced the peroxide number to a value of 2 or less at recoveries in excess of 95%. Concurrently, the adsorbents worked to affect a substantial reduction in the color of the olefinic mixture. The total result is that the olefinic product after treatment with adsorbents is safer, chemically more tractable, and commercially of more desirable appearance.

We claim as our invention:

1. A process for reducing the peroxide number and color of internal aliphatic olefins possessing a carbon content of from about 8 carbon atoms to about 20 carbon atoms which process comprises contacting said internal aliphatic olefins with an adsorbent selected from the group consisting of charcoal, alumina, silica, diatomaceous earth, montmorillonite clays and kaolin minerals at a temperature of from about 10° C. up to about 80° C., wherein said adsorbent is present in a quantity by weight of from about 0.5% to about 10% per unit weight of said internal aliphatic olefins and separating said internal aliphatic olefins of reduced peroxide number and improved color from said adsorbent.

2. The process of claim 1 wherein said olefins are formed by the oligomerization of olefins containing from about 3 to about 6 carbon atoms.

* * * * *